(12) United States Patent
Heitz et al.

(10) Patent No.: US 10,244,968 B2
(45) Date of Patent: Apr. 2, 2019

(54) METHOD AND SYSTEM FOR TRACKING A PERSON IN A MEDICAL ROOM

(71) Applicant: GENERAL ELECTRIC COMPANY, Schenectady, NY (US)

(72) Inventors: Renaud Heitz, Paris (FR); Daniel Gannat, Montigny le bx (FR); Regis Vaillant, Villebon sur Yvette (FR); Vincent Jonas Bismuth, Paris (FR); Bruno Vigan, Vauhallan (FR); Romain Moulin, Paris (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/537,472

(22) PCT Filed: Dec. 15, 2015

(86) PCT No.: PCT/US2015/065766
§ 371 (c)(1),
(2) Date: Jun. 19, 2017

(87) PCT Pub. No.: WO2016/109182
PCT Pub. Date: Jul. 7, 2016

(65) Prior Publication Data
US 2018/0000383 A1 Jan. 4, 2018

(30) Foreign Application Priority Data
Dec. 30, 2014 (GB) .................................... 1423355.5

(51) Int. Cl.
*A61B 5/11* (2006.01)
*A61B 6/00* (2006.01)
(Continued)

(52) U.S. Cl.
CPC .......... *A61B 5/1113* (2013.01); *A61B 5/0046* (2013.01); *A61B 6/10* (2013.01);
(Continued)

(58) Field of Classification Search
CPC ....... A61B 5/1113; A61B 5/0046; A61B 6/10; A61B 6/547; A61B 6/102; G06F 19/00
See application file for complete search history.

(56) References Cited

U.S. PATENT DOCUMENTS

2007/0255111 A1 11/2007 Baldus et al.
2008/0162046 A1 7/2008 Kotian et al.
(Continued)

FOREIGN PATENT DOCUMENTS

EP 1253438 A2 10/2002
WO 9739683 A1 10/1997
(Continued)

OTHER PUBLICATIONS

International Search Report and Written Opinion for PCT/US2015/065766, dated May 31, 2016, 14 pages.
(Continued)

*Primary Examiner* — Brian A Zimmerman
*Assistant Examiner* — Sara B Samson

(57) ABSTRACT

A method for tracking the position of a person in an environment, such as a medical room, relative to a medical device is presented. The method comprises identifying the position of a medical device in the environment, providing a mobile device in the vicinity of a person in the environment, the mobile device configured to follow movement of the person in the environment, and identifying the position of the mobile device in the environment by using at least one stationary device. Further, the method comprises using a processor to process data relating to the position of the mobile device in the environment to obtain an expected
(Continued)

position of the person in the environment, data relating to the position of the medical device in the environment, and data relating the expected position of the person in the environment to obtain an expected relative position of the person with respect to the medical device.

17 Claims, 3 Drawing Sheets

(51) Int. Cl.
    *A61B 6/10*     (2006.01)
    *A61B 5/00*     (2006.01)
    *G06F 19/00*     (2018.01)

(52) U.S. Cl.
    CPC .............. *A61B 6/547* (2013.01); *G06F 19/00* (2013.01); *A61B 6/102* (2013.01)

(56) References Cited

U.S. PATENT DOCUMENTS

| | | | | |
|---|---|---|---|---|
| 2008/0258929 A1* | 10/2008 | Maschke | ............... | A61B 6/102 340/686.1 |
| 2009/0119124 A1* | 5/2009 | Kambaloor | ............ | G06Q 50/22 705/2 |
| 2009/0257564 A1* | 10/2009 | Kito | ................... | A61B 6/4283 378/206 |
| 2010/0056905 A1 | 3/2010 | Anderson | | |
| 2010/0188231 A1 | 7/2010 | Winter et al. | | |
| 2012/0004518 A1 | 1/2012 | D'Souza et al. | | |
| 2013/0024382 A1 | 1/2013 | Dala et al. | | |
| 2013/0141233 A1 | 6/2013 | Jacobs et al. | | |
| 2013/0184005 A1* | 7/2013 | Hieronimi | ............. | G01S 5/0247 455/456.1 |
| 2014/0133627 A1* | 5/2014 | Sakuragi | ............... | A61B 6/4429 378/62 |
| 2014/0247918 A1* | 9/2014 | Kang | ................... | A61B 6/4452 378/62 |
| 2016/0113728 A1* | 4/2016 | Piron | ................. | A61B 17/3421 606/130 |
| 2017/0360514 A1* | 12/2017 | Eichler | ................. | A61B 34/20 |

FOREIGN PATENT DOCUMENTS

| | | |
|---|---|---|
| WO | 2004/093023 A2 | 10/2004 |
| WO | 2015044058 A1 | 4/2016 |

OTHER PUBLICATIONS

Combined Search and Exam Report for corresponding GB Appln. No. 1423355.5, dated Jun. 18, 2015, 5 pages.

Extended European Search Report and Opinion issued in connection with corresponding EP Application No. 15875954.8 dated May 18, 2018.

* cited by examiner

METHOD AND SYSTEM FOR TRACKING A PERSON IN A MEDICAL ROOM

CROSS-REFERENCE TO RELATED APPLICATIONS

This application is a US National Phase filing under 35 U.S.C. § 371 (c) of co-pending International Application No. PCT/US2015/065766, filed on Dec. 15, 2015, which claims priority to GB Application No. 1423355.5, filed on Dec. 30, 2014; the above-referenced applications are incorporated herein by reference in their entireties.

BACKGROUND

Medical devices, such as imaging devices are often used in combination with many other medical devices. These other devices are, for example, devices provided with a screen for monitoring data. Other devices include medical instruments like injectors or support devices such as tables. In order to operate the variety of devices in a medical room efficiently, there appears to be need to an improve tracking of the relative position of patients and staff with respect to the medical devices, during the use of such medical devices. Regarding patients, in the prior art, it is suggested to locate the medical device with respect to the patient's bed. This approach will have as an effect that if a patient moves on its bed, no adjustment is made with respect to the amended relative position of the medical device and the patient. With respect to staff members, for the operation of medical devices, the relative position between the staff members and the devices is not used to improve the use of the devices.

SUMMARY OF THE INVENTION

In one aspect, the present disclosure is directed to a method for tracking the position of a person with respect to a medical device in an environment, such as a medical room by means of a mobile device, wherein the environment is provided with at least one stationary device configured to identify the position of said mobile device in said environment. The method comprises identifying the position of the medical device in the environment, receiving the person in the environment, providing the mobile device in the vicinity of the person, the mobile device configured to follow any movement of the person in the environment, identifying the position of the mobile device in the medical room by means of the at least one stationary device, and processing data relating to the position of the mobile device in the environment by means of a processor to obtain an expected position of the person in the environment. The method further comprises processing data relating to the position of the medical device in the environment and data relating the expected position of the person in the environment by means of a processor to obtain an expected relative position of the person with respect to the medical device.

In another aspect, the disclosure relates to a computer readable medium storing computer-executable instructions, which when executed by a computer, cause the computer to perform the method according the present disclosure.

In yet another aspect, the disclosure relates to a system for tracking the position of a person with respect to a medical device in an environment, such as a medical room, using a mobile device. The system comprises a medical device, configured to be used in the environment, at least one stationary device positioned in the environment and configured to identify a mobile device, and a mobile device configured to be identified by means of the stationary device to allow the identification of the position of the mobile device in the environment. The mobile device is further configured to be positioned in the vicinity of a person and to follow any movement of the person in the environment. The system further comprises a computer processor connected to the stationary device and the medical device, and configured to process data relating to the position of the mobile device in the environment to obtain an expected position of the person in the environment. The processor is further configured to process data relating to the position of the medical device in the environment and data relating the expected position of the person in the environment to obtain an expected relative position of the person with respect to the medical device.

At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

In the present disclosure, the wording "medical room" is used to indicate the environment wherein the medical device and the mobile device for tracking a person in the medical room are used. This "medical room" wherein the medical device and the mobile device are used can depend on the type of medical device that is concerned. According to the present disclosure the medical device and the mobile device are used in an environment which allows the identification of their respective position in said "medical room". According to an embodiment of the invention it is possible that the position and the orientation of both the medical device and the mobile device can be determined in the "medical room".

In the present disclosure, the word "mobile device" makes reference to a device which can be moved inside the medical room. The mobile device can be attached to a person or to a support whereon a person is present. The purpose of the mobile device is to provide an element of which the position can be identified in an automated manner. The mobile device is adapted to follow any movement of the person or the support to which the mobile device is attached, in the medical room.

Figure 1:
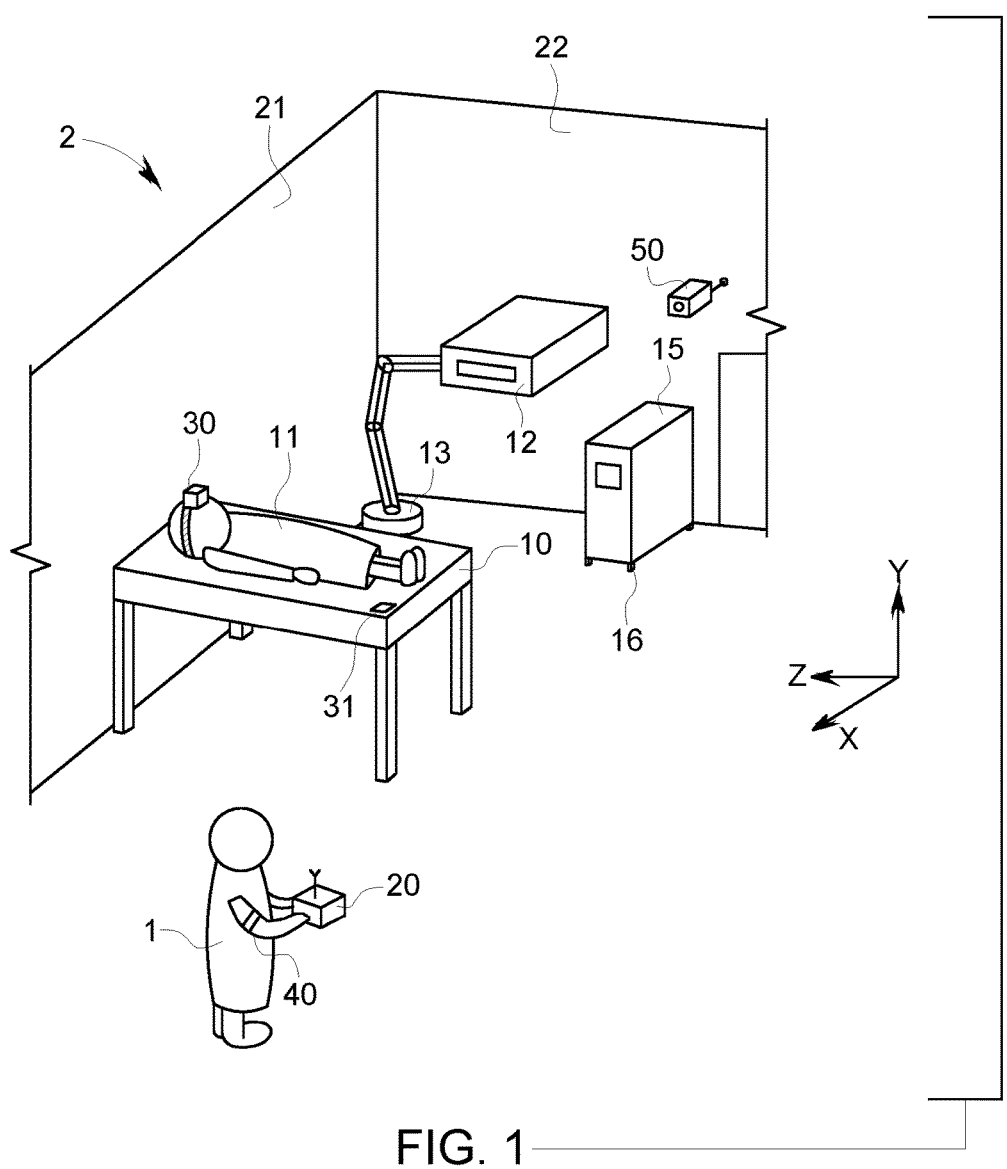
FIG. 1 is a diagrammatic illustration of an environment, such as a hospital medical room wherein a patient and an operator interact with a variety of medical devices.

FIG. 1 is a diagrammatic illustration of a medical room 2 wherein a variety of medical devices is operated by an operator 1. The medical room 2 is for example a medical room in a medical institution, like a hospital. The operator 1 is for example a medically skilled person like a doctor or an assistant.

In the medical room 2 a first device 10 is present which is used as a table or support for supporting a person 11. This person 11 could be a patient of which physiological parameters of any type need to be obtained. In the medical room 2 a first medical device 12 is present for obtaining physiological parameters of a certain type. In order to operate the medical device 12 the operator 1 uses an input device 20. This input device 20 is, for example, a joystick which is connected to a control unit which is part of the medical device 12 or connected to the medical device 12. The input device 20 can be used to operate the medical device 12 and will allow, a.o., to control of the movement of the medical device 12 with respect to the patient 11. The input device 20 can be a wireless input device which can communicate, using a wireless communication protocol, with a medical device 12 or a control device connected to the medical device 12.

In the medical room 2 according to FIG. 1 a further medical device 15 is present which can be operated using a further input device (not shown). This further input device could be similar to the input device 20 or could be of a different type. The table 10 could also be provided with an input device, for moving the bed and the patient 11 in the medical room 2. It will be understood that the larger the number of medical devices to be operated by the operator 1, the more complicated the operation of the different devices becomes, especially if the operator 1 only uses the different medical devices 12, 15 occasionally. The operation of the medical devices is even more difficult if the use of the medical device 12, 15 requires precise positioning of the device 12, 15 with respect to the patient 11. The operation of the medical devices 12, 15 can also be influenced by the presence of staff in the medical 2, which may hinder movement of the medical devices 12, 15 in the medical room 2.

An instruction provided by means of the input device 20 can be used to operate medical device 12. A first instruction could, for example, relate to a required movement of the medical device 12 with respect to the person 11 in order to position the medical device 12 correctly with respect to said person 11. A second instruction could include a specific action to be executed by the medical device 12 in order to measure physiological parameters of the person 11. This specific action could include obtaining an image by means of an imaging device or exposing a body part to a certain determined quantity of X-ray in case of an X-ray device.

In order to use the medical devices 12, 15 adequately, the position of both the medical device 12, 15 and the patient 11 in the medical room 2 should be known. The position of the medical device 12, 15 can be obtained in any appropriate manner. In case the medical device 12 has a fixed support 13, the position of the medical device could be taken with reference to this support 13. In case the medical device 15 can be moved in the medical device by means of wheels 16, for example, the position of the medical device 15 could be obtained by means of a reference provided by for example one of the walls 21, 22 of the medical room 2.

The position of the patient 11 is obtained by means of a mobile device 30. In the example of FIG. 1, the mobile device is fixed to the forehead of the patient 11. The mobile device 30 could be fixed to any appropriate part of the body of the patient 11, as long as the identification of the position of the mobile device 30 allows for obtaining an expected position of the body of the patient 11.

The mobile device 30 is specifically adapted to allow the identification of the position of the mobile device by means of a stationary device 50. Once the position of the mobile device 30 has been obtained, an expected position of the body of the patient 11 can be deduced. According to the example of FIG. 1, only one stationary device 50 is used to identify the position of one mobile device 30. Alternatively, a plurality of stationary devices 50 could be used. Similarly, a plurality of mobile devices 30 could be used to indicate the position of the patient 11 in the medical room 2. The plurality of mobile devices 30 could be attached to different body parts of the patients 11.

As shown in FIG. 1, in addition to or in stead of a mobile device 30 attached to the patient 11, a further mobile device 31 could be attached to the table 10 on which the patient 11 is supported. The mobile device 31 is positioned close to the body of patient 11 and could comprise a pressure sensor and a single or a plurality of mobile devices 31 could be used to detect the position of the patient 11 on the table 10, or on a mattress positioned on the table 10.

To allow the identification of staff members in the medical room 2, the operator 1 is provided with a mobile device 40. In the example of FIG. 1, the mobile device 40 has the form of a bracelet fixed to the upper arm of the operator 1. In stead of a single mobile device 40, a plurality of mobile devices 40 could be used to help identifying the position of staff members 1 in the medical room 2.

The different mobile devices 30, 31, 40 used for tracking the position of a person in the medical room 2 could have different forms and shapes and could be adapted to be allow identification of the mobile devices by means of the stationary device 50 in different manners. According to a first example of the disclosure, the mobile device will as small as possible. The smaller the mobile devices 30, 31, 40 are, the less inconvenience they will cause both for the person using the devices 30, 31, and 40 and for operating the medical devices 12, 15. According to an example of the disclosure the mobile devices 30, 31, 40 will be a passive device which does not need any wiring to allow either power or signal transfer. According to an example of the disclosure the mobile devices do not need a free line of sight in order to be identified by the stationary device.

The mobile device 30, 31, 40 used to allow the tracking of a person in the medical room 2 and the stationary device 50, can be adapted to allow the localization by means of the translations in three directions, schematically indicated by the axis X, Y, Z. Alternatively, the mobile device 30, 31, 40 and the stationary device 50 can be adapted to allow localization including the three translations (X, Y, Z) in combination with three possible rotations.

According to a further example of the invention, the mobile devices 30, 31, 40 could be adapted to communicate with the stationary device 50 by means of any adapted wireless communication protocol. It should be noted that the mobile devices 30, 31, 40 could be adapted to allow the identity of the mobile devices. This means that the stationary device 50 is not only able to obtain information about where the different mobile devices 30, 31, 40 are in the medical room 2, but also which mobile devices 30, 31, 40 are present in the specific locations in the medical room 2.

Figure 2:
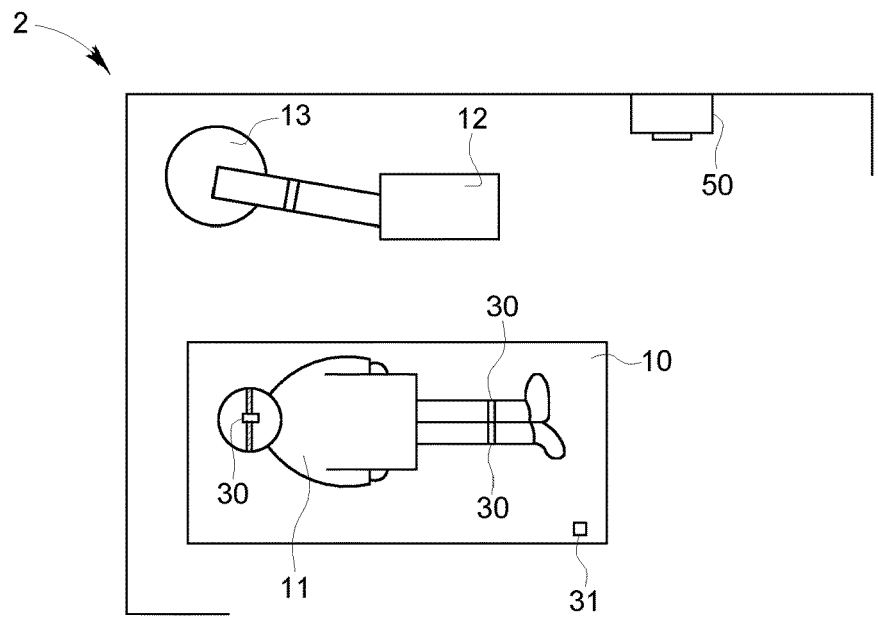
FIG. 2 is a diagrammatic illustration, in top view, of an environment, such as a hospital medical room wherein a patient is positioned on a support and at least a first medical device is used.

A first possible use of the method and the system according to the disclosure is shown in FIG. 2. FIG. 2 schematically shows medical room 2 in top view. The patient 11 is provided with a first mobile device 30 attached to the forehead. Two further mobile devices 30 are attached to the legs of the patient 11. The stationary device 50 is used to localize the position of the respective mobile devices 30. Once the position of the mobile devices 30 is known, the data relating to the respective positions can be forwarded to a processor. The processor can be used to obtain an expected position of the patient 11 in the medical room 2. The information relating the position of the mobile devices can be completed by means of a computer model of the patent 11. This computer model can be a 3D patient model which can be fitted on the respective positions for the mobile devices 30. The result of this is that the patient position and the position of the different body parts of the patient 11 are known in the medical room 2.

The fact that the patient position is known in the medical room 2 will allow an improvement of medical procedures executed in the medical room 2. In order to allow the improvement, according to an example, the position of the medical device 12 in the medical room 2 should also be identified by means of any suitable manner. In a first example the position of the patient 11 can be used when moving the medical device 12 towards the patient 11. Since both the patient position and the position of the medical device 12 are known a relative position between the patient 11 and the medical device 12 can be obtained. When moving the medical device 12 towards the patient 11, the known relative position of the medical device 12 with respect to the patient 11 can be used to avoid patient collision. A further example relates to the positioning of the medical device 12 with respect to the patient 11. The known relative position of the medical device 12 with respect to the patient can be used to correctly position the medical device with respect to the patient 11, while the positioning is no longer operator dependent.

A further example of the use of the known relative position between the patient 11 and the medical device 12 is the fact the operating mode of the medical device 12 can be adapted to the patient anatomy in the field of view. This is, for example, useful in case the medical device is adapted for image acquisition. The use of the medical device 12 can also be adapted to interventional tools that are present inside the patient. These tools include, for example, a balloon. With the patient 11 position being known, instructions can be generated to find the exact position of these tools inside the patient 11.

The method and system according to the present disclosure can be used to manage the use of a medical device 12 at a first instance and at subsequent further instances. As an example reference is made to the use of an X-ray device. The patient position is obtained by means of the mobile devices 30. In case the mobile devices 30 are adapted to identify the identity of the mobile devices 30, a database can be created wherein the details of the patient 11 and the specific use of medical device 12 can be stored. If an X-ray device is used for a patient 11, the specific use of the X-ray device, including the X-ray dose and the body part of the patient receiving the X-ray dose can be stored. Prior to subsequent use of the X-ray device for the same patient 11, the database can be consulted to acquire data relating the X-ray doses used for the patient 11. This will allow, for example, to avoid the submission of an overdose of X-rays to a patient 11 or a patient body part. According to an example, the database is linked to the control device of the X-ray device to allow access to the database prior to using the device for a patient 11.

Figure 3:
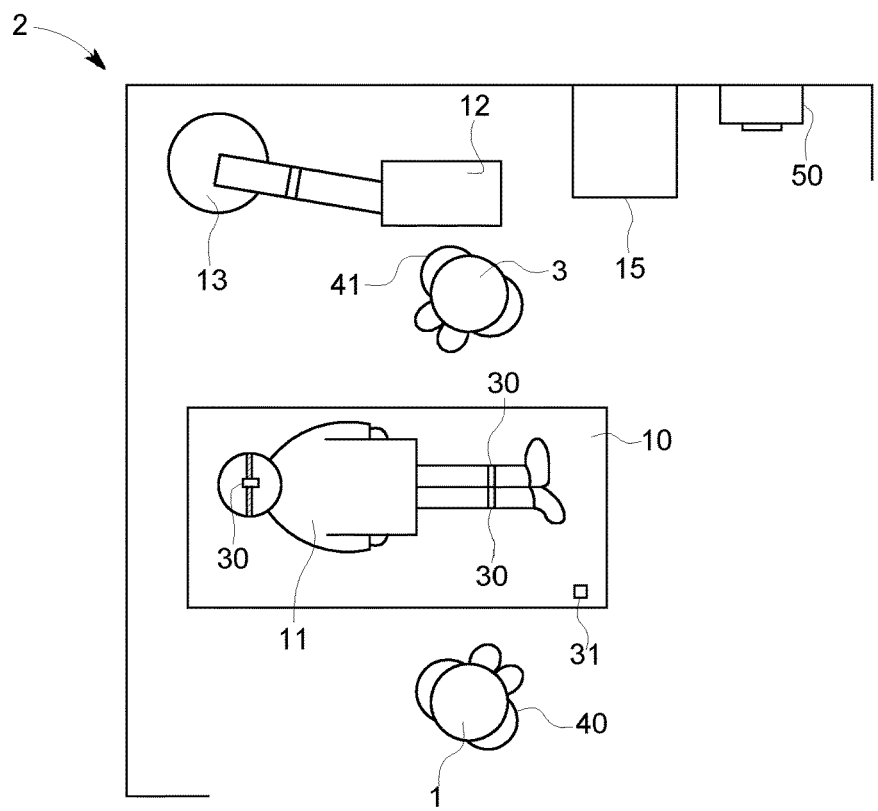
FIG. 3 is a diagrammatic illustration, in top view, of an environment, such as a hospital medical room wherein a patient and at least a first and a second staff member interact with at least a first and a second medical device.

A second possible use of the method and the system according to the disclosure is shown in FIG. 3. FIG. 3 schematically shows medical room 2 in top view. The patient 11 is provided with a first mobile device 30 attached to the forehead. Two further mobile devices 30 are attached to the legs of the patient 11 as described with reference to FIG. 2. In the medical room 2 a first member of staff 1 and a further member of staff 3 are present. The first member of staff 1 is provided with a mobile device 40, to allow the tracking of the staff member 1 inside the medical room 2. The second member of staff 3 is provided with a similar mobile device 41 to allow the tracking of the second member 3 of staff in the medical room 2. As described with respect to FIG. 2 the position of the medical devices 12, 15 can be obtained by means of any adapted device. Once the position of the staff members 1, 3 and the medical devices 12, 15 is known, this information can be used to obtain a relative position of the staff members 1, 3 with respect to the medical devices 12, 15. The relative position between the staff members 1, 3 and be used to improve medical procedures in the medical room 2.

A first exemplary use of the relative position between staff members 1, 3 and the medical devices 12, 15 is during movement of the medical devices 12, 15 in the medical room 2. When moving a medical device 12, 15 collisions between devices 12, 15 and staff members 1, 3 can be avoided. The information relating to the relative distance between the devices 12, 15 and the staff members 1, 3 can, for example, be used to adapt device trajectories, to decrease the travel speed of the devices 12, 15, to prevent the devices 12, 15 from moving or to provide a warning that a specific staff member 1, 3 prevents the medical device 12, 15 motion. With reference to FIG. 3, this warning could have the form of a message like: "staff member 3 prevents the device 15 from moving towards table 10".

A second exemplary use of the relative position between staff members 1, 3 and the medical devices 12, 15 helps to increase the safety of the staff members 1, 3 who are operating the medical devices 12, 15. As an example reference is made to the use of an X-ray device. In case the mobile devices 40, 41 are adapted to identify the identity of the mobile devices 40, 41 a database can be created wherein the details of the staff members 1, 3 and the specific use of the medical device 12, 15 can be stored. If an X-ray device is used in the presence of staff member 3, the specific use of the X-ray device, including the X-ray dose to which staff member 3 is exposed can be stored in the database. Prior to subsequent use of the X-ray device in the presence of the same staff member 3, the database can be consulted to acquire data relating the X-ray doses to which the staff member 3 has been exposed. This will allow, for example, to avoid the exposure of an overdose of X-rays to a staff member 3. A related use concerns the possibility to avoid the X-ray device from operating or the creation of an alarm if one or more staff members 1, 3 are in a high radiation area around the X-ray device.

A further possible use of the relative distance between the staff members 1, 3 and the medical devices 12, 15 is providing instructions for the displays which are used connected to the medical devices 12, 15. Parameters for the displays, such as, the contrast, intensity, the position of the display itself, or the display layout can be adapted to the staff positions. If the system detects that a specific device is present, the display can be adapted to allow part of the display to be used in connection with this device. For example, if an IVUS cart is pulled in the medical room 2, the display layout can be adapted to the room layout in that part of the display is reserved for the IVUS. Alternatively, a single display could be used for multiple medical devices, wherein the menus available on the display would depend on the proximity of staff members 1, 3 to with respect to the medical devices.

A further use of the method and the system according the disclosure is to adapt the operation of a medical device 12, 15 based on the position of a staff members 1, 3. For example, in case of an imaging device, image processing could be adapted to events in the medical room 2. This means, for example, that if it is noted that a staff member has put his hand on the injector, the image processing could be adapted to take into account the fact that a fluid has been injected in the patient 11.

A further use of the method and the system according the disclosure is to adapt the use of a medical room 2, based on staff positions. It is possible to monitor the position of the staff members 1, 3 with respect to the medical devices 12, 15. A virtual view of the room can be created, showing the position of both staff 1, 3 and medical devices 12, 15 continuously. The specific positions of staff members 1,3 and medical devices can be monitored to create statistics of specific medical procedures in the medical room 2. These statistics can be used to improve the efficiency of the medical procedures, for example, by enhancing the layout of the medical room 2 for future similar procedures. An objective could be to minimize the walking distance for staff members during interventions. Another objective could be to improve the working conditions, for example, by adapting the lightning set up in the medical room 2.

According to the present disclosure intuitive use of medical devices 12, 15 can be enhanced by the fact that an instruction for the medical device 12 comprises two elements. The first element of the instruction for the medical device 12 will be generated by means of the input device 20 wherein, in the example of FIG. 1, a movement of a joystick will generate an input signal relating to an instruction for the medical device 12 to move from a first towards a second position. The second element of the instruction is dependent of the staff position and the position of the medical 12 in the medical room 2. The information relating the position of the device in the medical room 2 and the relative position between the staff members 1, 3 and the medical devices 12, 15 can be used to complete the generated instruction.

A related use of the method and the system according to the disclosure is to guarantee the presence of at least a number of staff members 1,3 in the medical 2 to supervise the patient 11. For example, if the presence of at least one member of staff would be required an alarm signal could be produced if the stationary device is no longer capable to identify at least one mobile device 40, 41 of a staff member.

Figure 4:
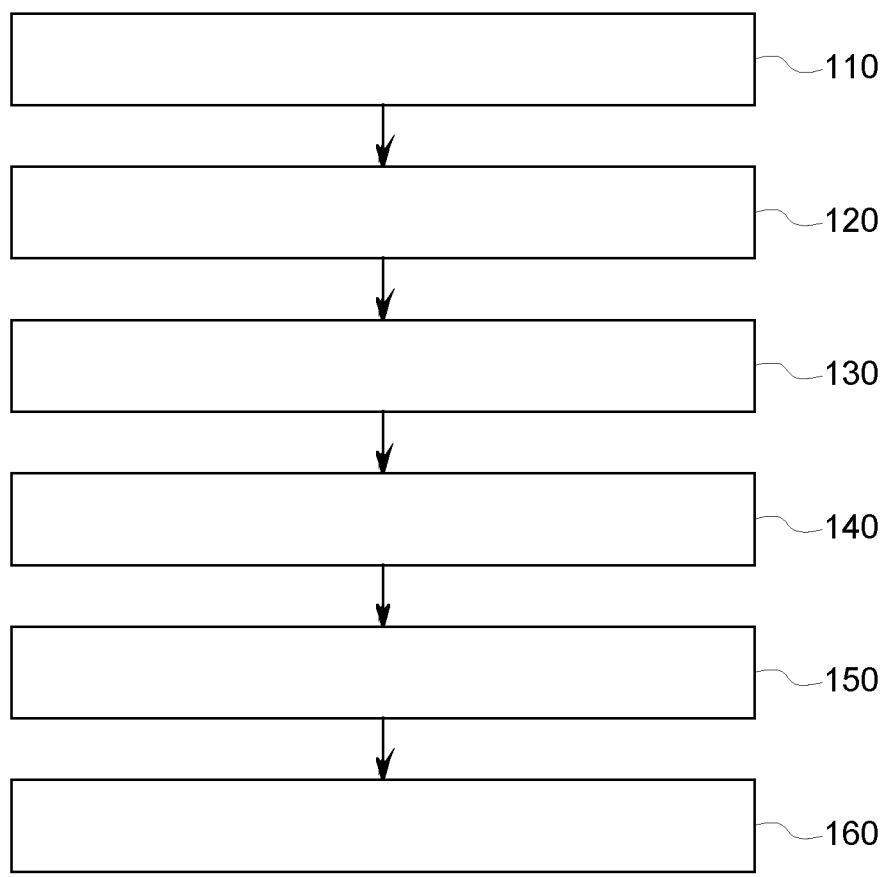
FIG. 4 shows a flow chart of an embodiment of the method according to the present disclosure.

FIG. 4 shows a flow chart of an embodiment of the method of the present disclosure. According to FIG. 4 in a first step 110 the position of the medical device in the medical room is identified.

In second step 120 a person is received in the medical room.

In a third step 130 a mobile device provided in the vicinity of the person, the mobile device being adapted to follow any movement of the person in the medical room.

In a forth step 140 the position of the mobile device in the medical room is identified by means of the at least one stationary device.

In a fifth step 150 data relating to the position of the mobile device in the medical room are processed by means of a processor to obtain an expected position of the person in the medical room.

In a sixth step 160 data relating to the position of the medical device in the determined environment and data relating the expected position of the person in the medical room are processed by means of a processor to obtain an expected relative position of the person with respect to the medical device.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. Method for tracking the position of a person in an environment relative to a medical device, comprising:
   providing a medical device in the environment;
   providing at least one stationary device in the environment, wherein the stationary resides in a fixed position in the environment;
   providing a first mobile device associates with a caregiver in the environment, and a second mobile device associated with a patient in the environment, the first and second mobile devices configured to follow any movement of the caregiver and patient in the environment;
   identifying the position of the medical device in the environment;
   identifying the position of the first and the second mobile devices in the environment using the at least one stationary device; and
   using a processor to process data relating to the position of the first and the second mobile devices in the environment to obtain an expected position of the caregiver and the patient in the environment, data relating to the position of the medical device in the environment, and data relating to the expected position of the caregiver and the patient in the environment to obtain an expected relative position of the caregiver and the patient respectively relative to the medical device.

2. The method according to claim 1, further comprising attaching the mobile device to the at least one of the caregiver and patient.

3. The method according to claim 1, further comprising:
   identifying the position and orientation of the medical device in the environment;
   identifying the position and orientation of the first and the second mobile devices in the environment; and
   using a processor to process data relating to the position and orientation of the mobile device in the environment to obtain an expected position and orientation of the caregiver and the patient in the environment, data relating to the position and orientation of the medical device, and data relating the expected position and orientation of the caregiver and the patient in the environment to obtain an expected relative position and orientation of the caregiver and the patient with respect to the medical device.

4. The method according to claim 1, further comprising:
   using a processor to create a patient model; and
   processing data relating to the position of the second mobile device in the environment in combination with the patient model to obtain the expected position of the patient in the environment.

5. The method according to claim 1, further comprising using a processor to process data relating to the position of the medical device in the environment and data relating the expected position of the caregiver and the patient in the environment to obtain an expected relative position of the person with respect to the medical device in real time.

6. The method according to claim 1, further comprising using the obtained expected relative position of the caregiver and the patient with respect to the medical device to generate an instruction for the medical device.

7. The method according to claim 6, further comprising positioning the medical device with respect to the caregiver and the patient using the obtained expected relative position of the caregiver and the patient with respect to the medical device.

8. The method according to claim 1, further comprising:
determining a threshold value relating to a maximum distance between the medical device and at least one of the caregiver and the patient;
comparing the distance between the medical device and the caregiver and the patient with the threshold value relating to a maximum distance between the medical device and the caregiver and the patient, respectively; and
generating a control signal to operate the medical device if the distance between at least one of the caregiver and the patient and the medical device is equal or below the threshold value.

9. The method according to claim 1, further comprising:
providing the first and the second mobile devices with an identity;
linking the identity of the mobile devices with the caregiver and the patient, respectively;
creating a database comprising data relating to both the identity of the mobile devices and the caregiver and the patient;
establishing communication between the mobile devices and the at least one stationary device to thereby generate a communication signal;
using the communication signal to determine the identity of the mobile devices and the caregiver and the patient, respectively;
using the medical device; and
updating the database by entering data relating to the use of the medical device in the database.

10. The method according to claim 9, further comprising:
generating an instruction for the medical device;
consulting the database to review the instruction for the medical device in view of the content of the database; and
review of the instruction, prior to sending of the instruction to the medical device.

11. The method according to claim 1, further comprising using the obtained expected relative position of the caregiver and the patient with respect to the medical device to generate an instruction relating the use of the environment.

12. The method according to claim 1, wherein the environment is a medical room.

13. The method according to claim 1, wherein the patient is lying on a table.

14. Amended System for tracking the position of a person with respect to a medical device in an environment, the system comprising:
a medical device usable in the environment;
at least one stationary device positioned in a fixed location in the environment and configured to identify the position of a mobile device;
first and second mobile devices configured to at least (i) be identified by the stationary device to allow an identification of the position of the mobile device in the environment, (ii) be positioned in the vicinity of a caregiver and the patient, and (iii) follow any movement of the caregiver and the patient in the environment; and
a computer processor connected to the stationary device and the medical device and configured to process data relating to the position of the mobile device in the environment to obtain an expected position of the caregiver and the patient in the environment, the computer processor further configured to process data relating to the position of the medical device in the environment and relating the expected position of the caregiver and the patient in the environment to obtain an expected relative position of the caregiver and the patient respectively relative to the medical device.

15. The system according to claim 14, wherein the environment is a medical room.

16. The system according to claim 14, wherein the patient is positioned on a table.

17. A non-transitory computer readable medium storing computer-executable instructions, which, when executed by a computer cause the computer to perform the method of claim 1.

* * * * *